United States Patent [19]

Moran et al.

[11] Patent Number: 4,847,486

[45] Date of Patent: Jul. 11, 1989

[54] ELECTRO-OPTICAL ALERTNESS MONITORING APPARATUS

[75] Inventors: Dan Moran, Ramat Chen; Yonatan Gerlitz, Herzlia, both of Israel

[73] Assignee: Rasaat, Ramat Gan, Israel

[21] Appl. No.: 163,362

[22] Filed: Mar. 2, 1988

[30] Foreign Application Priority Data

Mar. 18, 1987 [IL] Israel .................................. 81928

[51] Int. Cl.$^4$ ........................ G01V 9/04; G06M 7/00
[52] U.S. Cl. .................................. 250/221; 250/235
[58] Field of Search ............... 250/203 R, 221, 222.1, 250/235; 356/1, 4, 141, 152

[56] References Cited

U.S. PATENT DOCUMENTS

| 2,724,109 | 11/1955 | Skolnick et al. | 340/279 |
|---|---|---|---|
| 3,379,885 | 4/1968 | Nork | 250/83.3 |
| 3,863,262 | 1/1975 | Crofut et al. | 354/5 |
| 4,111,555 | 9/1978 | Ellis | 356/141 |
| 4,257,688 | 3/1981 | Matsumura | 351/210 |
| 4,397,531 | 8/1983 | Lee | 351/210 |
| 4,475,814 | 10/1984 | Marche | 356/138 |
| 4,528,989 | 7/1985 | Weinblatt | 351/210 |
| 4,541,697 | 9/1985 | Remijan | 351/205 |
| 4,625,329 | 11/1986 | Ishikawa et al. | 382/1 |
| 4,625,337 | 12/1986 | Zahn | 2/82 |
| 4,702,575 | 10/1987 | Breglia | 351/210 |
| 4,720,189 | 1/1988 | Heynen et al. | 351/210 |
| 4,744,648 | 5/1988 | Kato et al. | 351/211 |

Primary Examiner—David C. Nelms
Assistant Examiner—William L. Oen
Attorney, Agent, or Firm—Ladas & Parry

[57] ABSTRACT

Apparatus for monitoring the eye of a subject comprising: apparatus for directing infra-red radiation at the eyes of a subject; apparatus for sensing infra-red radiation retroreflected by the retina through the cornea of the subject; and apparatus for providing a sensible output indication in the absence of expected received retroreflected radiation, indicating the closing of the subject's eyes or direction of his eyes outside of a desired angular region.

19 Claims, 2 Drawing Sheets

ELECTRO-OPTICAL ALERTNESS MONITORING APPARATUS

FIELD OF THE INVENTION

The present invention relates to electro-optical alertness monitoring apparatus and more particularly to apparatus for monitoring the eyes of an operator.

BACKGROUND OF THE INVENTION

Various types of apparatus have been proposed for maintaining alertness of drivers and operators of machinery. U.S. Pat. Nos. 2,724,109 and 3,863,262 to Skolnick et al describe a sleep inhibitor for automobile drivers wherein light from a lamp is reflected from the driver's eyeball in order to activate an alarm when the eyeball is covered by the eyelid for more than a predetermined time. U.S. Pat. No. 3,379,885 to Nork describes a sight switch employing an infrared source and sensor which distinguishes between reflections from the white of the eyeball and the iris. Two other U.S. Pat. Nos. 4,397,531 and 4,625,337, use relatively expensive two dimensional image scanners and very heavy software to analyze the image.

SUMMARY OF THE INVENTION

The present invention seeks to provide improved apparatus for monitoring operator alertness. There is thus provided in accordance with a preferred embodiment of the present invention apparatus for monitoring the eye of a subject comprising:

apparatus for directing infra-red radiation at the eyes of a subject;

apparatus for sensing infra-red radiation retroreflected by the retina through the cornea of the subject; and apparatus for providing a sensible output indication in the absence of expected received retroreflected radiation, indicating the closing of the subject's eyes or direction of his eyes outside of a desired angular region.

Additionally in accordance with a preferred embodiment of the invention there is provided scanning means for causing the apparatus for directing and the apparatus for sensing to scan a given angular region.

BRIEF DESCRIPTION OF THE DRAWINGS

The present invention will be understood and appreciated more fully from the following detailed description, taken in conjuction with the drawings in which.

DETAILED DESCRIPTION OF A PREFERRED EMBODIMENT

Figure 1:
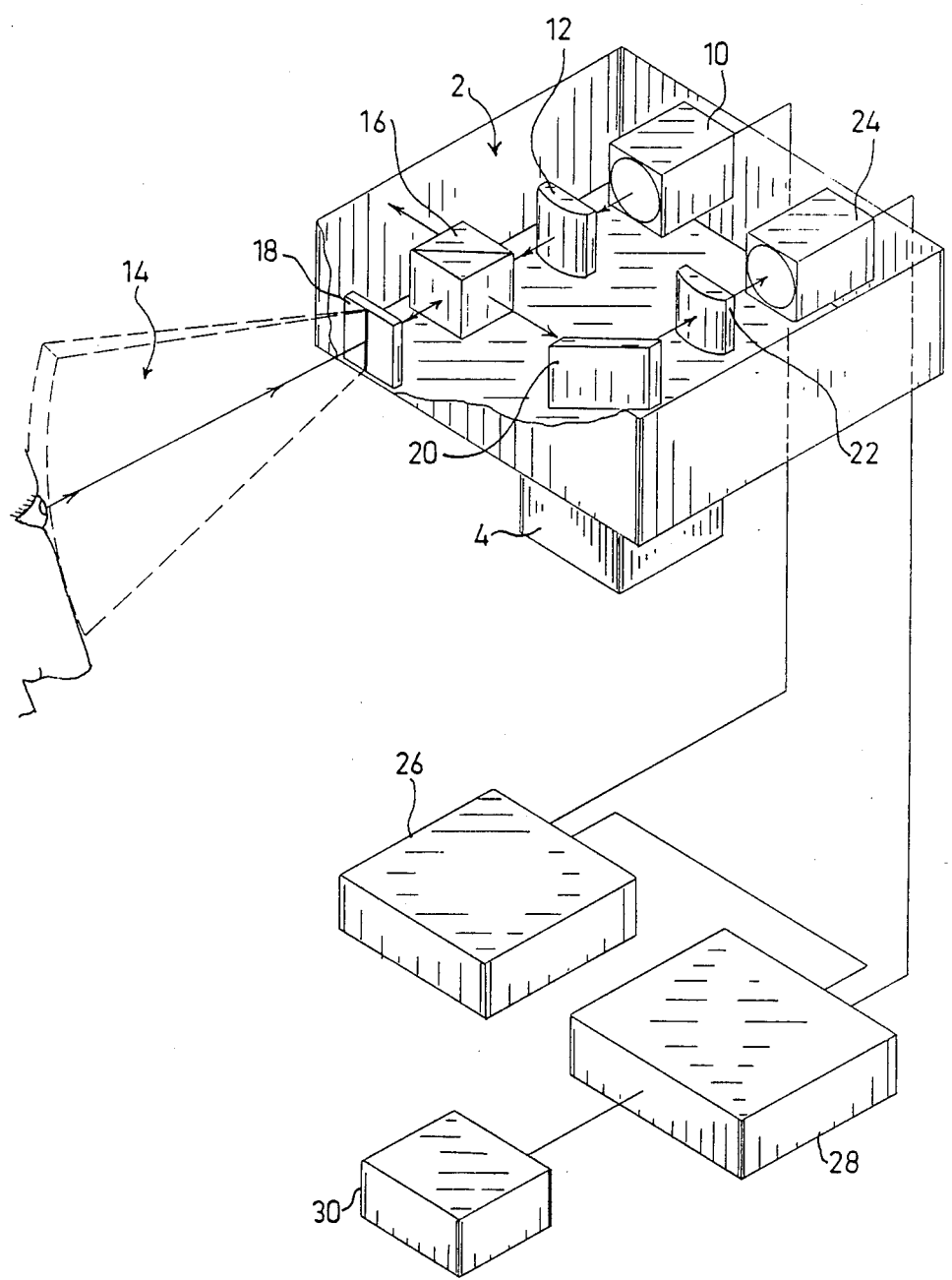
FIG. 1 is a partially pictorial-partially block diagram illustratin of apparatus for maintaining alertness constructed and operative in accordance with a preferred embodiment of the present invention.

Reference is now made to FIG. 1, which illustrates a preferred embodiment of the present invention including scanning platform 2 which is typically mounted and driven by means of a motor 4 for scanning rotation in a horizontal plane with respect to a reference mounting surface, such as the dashboard of a vehicle. A radiation source 10, is mounted onto platform 2, typically comprises a laser diode or an infrared emitting diode and emits radiation via a collimating lens 12, such as a cylindrical lens, so as to define a fan 14 of radiation disposed typically in a vertical plane.

The radiation output via collimating cylindrical lens 12 typically passes through a beam splitter 16 of conventional construction, which is operative to transmit a part of the beam through an IR filter 18, and to reflect the remainder.

Most of the light transmitted in fan 14 via filter 18 is reflected in a diffuse manner from the various surroundings. Light, within a given range of angles, impinging on the retina through the cornea of an operator's eye is retroreflected back in the direction from which it impinged on the cornea.

Retroreflected light received via the cornea impinges on a beam splitter 16 via filter 18 and is reflected by beam splitter 16, via a mirror 20 and a cylindrical or convex lens 22 to an infra-red detector 24, such as a photovoltaic silicon PN detector.

It is appreciated that all of the apparatus described above is mounted onto scanning platform 2.

Figure 2:
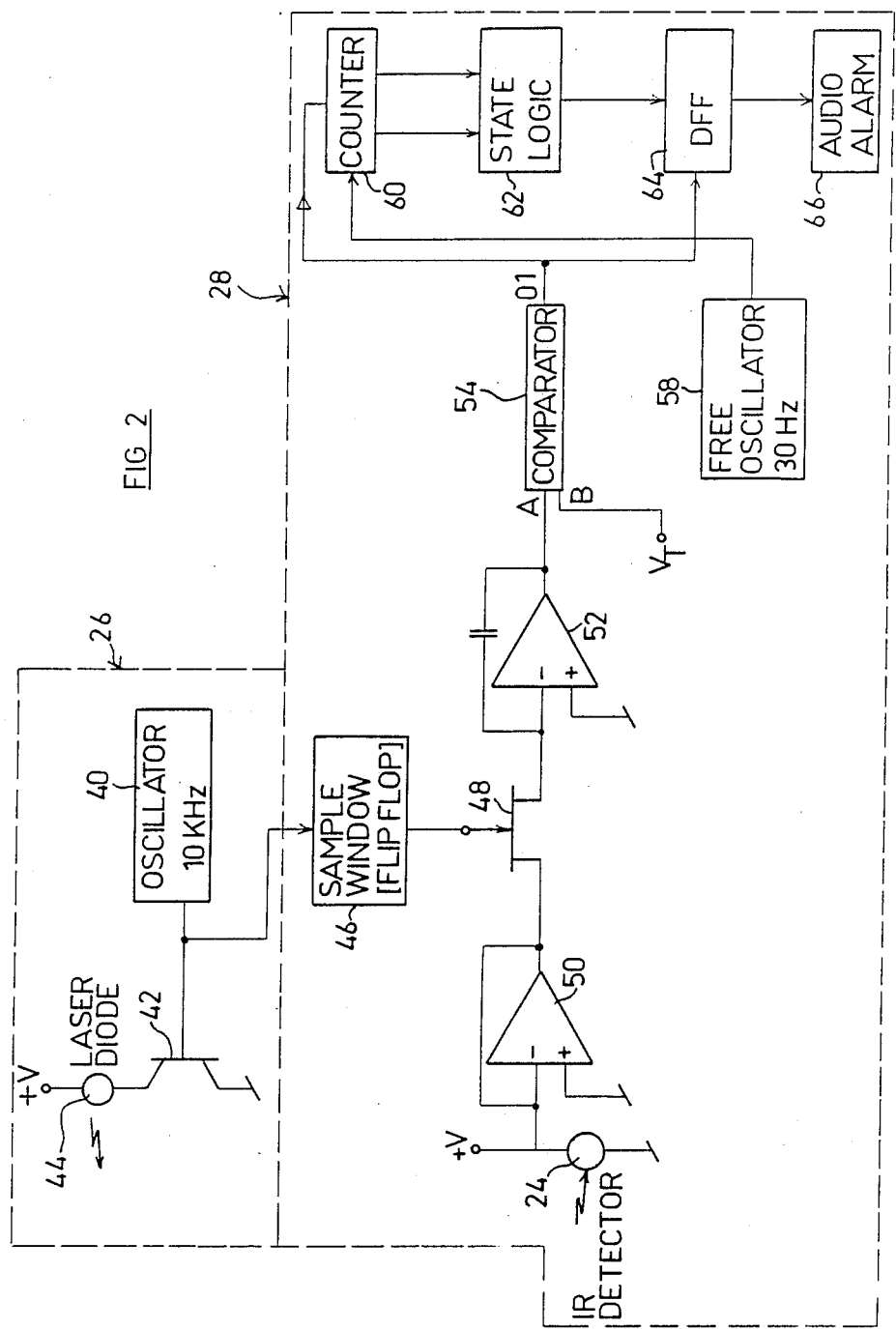
FIG. 2 is a partially schematic, partially block diagram, illustration of electronic circuitry useful in the present invention.

Radiation source 10 receives electrical power from emitter electronic circuitry 26, which is illustrated in FIG. 2, causing source 10 to transmit IR pulses at high frequency or in a continuous wave form.

When the operator's eye is directed within a suitable range of directions with respect to the radiation source, a retroreflected IR pulse train or continuous wave, as the case may be, is received by detector 24 and transmitted to detector electronic circuitry 28, which is illustrated in FIG. 2. This circuitry receives timing inputs from emitter electronic circuitry 26 and senses when anticipated retroreflected signals are not received within a predetermined time range. The absence of such retroreflected signals may indicate that the operator has closed his eyes, or looked outside of a predetermined permitted viewing range. When appropriate, circuitry 28 produces an alarm indication to a warning device 30, such as an audio alarm.

Operation of the warning device 30 may be terminated when the retroreflected light is once again received by detector 24.

Reference is now made to FIG. 2 which illustrates electronic circuitry employed in the apparatus of FIG. 1. An oscillator 40, typically operating at 10 KHz. provides an output to a power transistor 42, which provides a desired pulse output to a laser diode 44, which serves as radiation source 10 (FIG. 1).

The output of oscilator 40 is also provided via a flip flop circuit 46 to the base of transistor 48, which receives the output of IR detector 24 (FIG. 1) via an operational amplifier 50. Transistor 48 thus acts as a switch, permitting the output from operational amplifier 50 to pass only when it is received within a predetermined coincidence time of the transmission of an IR pulse by laser diode 44, thereby to prevent false detection due to spurious IR sources.

The output from transistor 48 is supplied via an operational amplifier 52 to a comparator 54, which compares it with a predetermined reference and provides a RESET input to a counter 60 and to a DFF circuit 64. A free oscillator 58, typically operating at 30 Hz provides a clocking input to counter 60.

The RESET input is provided by comparator 54 when retroreflected radiation is sensed by detector 24. Should counter 60 count up to a predetermined threshold count without being reset in response to detection of retroreflected radiation, such count output causes state logic circuitry 62, which receives counter outputs, to activate an alarm 66, such as an audio alarm, via the DFF circuitry 64.

DFF circuitry 64 is operative to terminate the operation of alarm 66, when it receives the RESET signal, indicative of sensed retroreflected radiation.

It will be appreciated by persons skilled in the art that the present invention is not limited by what has been particularly shown and described hereinabove. Rather the scope of the present invention is defined only by the claims which follow.

We claim:

1. Apparatus for monitoring the eye of a subject comprising:
   means for directing radiation at the eyes of a subject;
   means for sensing radiation retroreflected by the retina through the cornea of an eye of the subject;
   scanning means for causing said means for directing and said means for sensing to scan a given angular region in at least one direction; and
   means for providng a sensible output indication in the absence of expected received retroreflected radiation.

2. Apparatus according to claim 1 and wherein said radiation is outside the visible spectrum.

3. Apparatus according to claim 1 and wherein said radiation is infrared radiation.

4. Apparatus according to claim 2 and wherein said radiation is infrared radiation.

5. Apparatus according to claim 1 and wherein said scanning means are operative to scan in two orthogonal directions.

6. Apparatus according to claim 2 and wherein said scanning means are operative to scan in two orthogonal directions.

7. Apparatus according to claim 1 and wherein said scanning means are operative to scan in a horizontal plane.

8. Apparatus according to claim 2 and wherein said scanning means are operative to scan in a horizontal plane.

9. Apparatus according to claim 1 and wherein said means for directing comprise a collimating lens.

10. Apparatus according to claim 2 and wherein said means for directing comprise a collimating lens.

11. Apparatus according to claim 3 and wherein said means for directing comprise a collimating lens.

12. Apparatus according to claim 4 and wherein said means for directing comprise a collimating lens.

13. Apparatus according to claim 5 and wherein said means for directing comprise a collimating lens.

14. Apparatus according to claim 1 and wherein said means for sensing comprise a beam splitter and an infrared detector.

15. Apparatus according to claim 2 and wherein said means for sensing comprise a beam splitter and an infrared detector.

16. Apparatus according to claim 1 and wherein said means for providing include circuitry receiving inputs representing the timing of radiation outputs from said means for directing and inputs representing the timing of retroreflected radiation received by said means for sensing, for providing an alarm actuation output signal.

17. Apparatus according to claim 2 and wherein said means for providing include circuitry receiving inputs representing the timing of radiation outputs from said means for directing and inputs representing the timing of retroreflected radiation received by said means for sensing, for providing an alarm actuation output signal.

18. Apparatus according to claim 1 and wherein said means for providing an sensible output indication in the absence of expected received retroreflected radiation is operative for indicating the closing of the operator's eyes or direction of his eyes outside of a desired angular region.

19. Apparatus according to claim 2 and wherein said means for providing an sensible output indication in the absence of expected received retroreflected radiation is operative for indicating the closing of the operator's eyes or direction of his eyes outside of a desired angular region.

* * * * *